United States Patent [19]

Brush et al.

[11] 4,342,686

[45] Aug. 3, 1982

[54] INTERMEDIATES FOR PREPARING 6-LOWER ALKYL-7,8-DIHYDROXY-1-PHENYL-2,3,4,5-TETRAHYDRO-1H-3-BENZAZEPINES

[75] Inventors: Charles K. Brush, Malvern; Joseph Weinstock, Phoenixville, both of Pa.

[73] Assignee: SmithKline Corporation, Philadelphia, Pa.

[21] Appl. No.: 206,428

[22] Filed: Nov. 13, 1980

Related U.S. Application Data

[60] Division of Ser. No. 972,296, Dec. 22, 1978, Pat. No. 4,265,889, which is a continuation-in-part of Ser. No. 903,325, May 5, 1978, abandoned, which is a continuation-in-part of Ser. No. 852,404, Nov. 17, 1977, Pat. No. 4,165,372.

[51] Int. Cl.$^3$ .................... C07D 223/16; A61K 31/55
[52] U.S. Cl. ............................. 260/239 BB; 424/274
[58] Field of Search .................................. 260/239 BB

[56] References Cited

U.S. PATENT DOCUMENTS 4,265,889  5/1981  Brush et al. .......................... 424/274

FOREIGN PATENT DOCUMENTS 555831  2/1967  Switzerland .................. 260/239 BB

*Primary Examiner*—David B. Springer
*Attorney, Agent, or Firm*—William H. Edgerton; Richard D. Foggio; Alan D. Lourie

[57] ABSTRACT

The preparation and use as intermediates is described for 7,8-dihydroxy-1-phenyl-2,3,4,5-tetrahydro-1H-3-benzazepines whose structures are characterized by having either an aralkyl or lower alkanoyl group at position 2 or an α-hydroxyalkyl or α-chloroalkyl group at position 6.

10 Claims, No Drawings

INTERMEDIATES FOR PREPARING 6-LOWER ALKYL-7,8-DIHYDROXY-1-PHENYL-2,3,4,5-TETRAHYDRO-1H-3-BENZAZEPINES

This is a divisional application of copending Ser. No. 972,296 filed Dec. 22, 1978 now U.S. Pat. No. 4,265,889, which is a continuation-in-part of our application Ser. No. 903,325 filed May 5, 1978, now abandoned, which is in turn a continuation-in-part of Ser. No. 852,404 filed Nov. 17, 1977, now U.S. Pat. No. 4,165,372.

This invention comprises a new group of dopaminergic compounds which are 1-phenyl-2,3,4,5-tetrahydro-1H-3-benzazepines whose structures have at least three substituents in the benz-ring of the nucleus one of which is a lower alkyl at the 6-position.

DESCRIPTION OF THE ART

Certain 1-phenyl-2,3,4,5-tetrahydro-1H-3-benzazepines have been described in Swiss Pat. No. 555,831, including certain general methods of preparation of the 1-phenyl-2,3,4,5-tetrahydro-1H-3-benzazepine ring system. However this reference discloses no specific 6-lower alkyl substitution in the structures and is a broad generic disclosure.

DESCRIPTION OF THE INVENTION

The structures of the compounds of this invention are specifically identified by having a branched or straight lower alkyl substituent of from 1–6 carbon atoms, such as a methyl, ethyl, propyl, isopropyl, butyl, isoamyl or hexyl group at the 6-position of the 1-phenyl-tetrahydro-3-benzazepine system in addition to hydroxy or derivatized hydroxy groups at both the 7- and 8-positions.

Exemplary of this new group of compounds are those represented by the following structural formula:

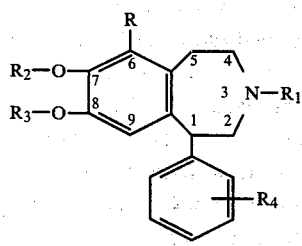

I in which:

R is lower alkyl of 1–6 carbon atoms preferably methyl or propyl;

$R_1$ is hydrogen, benzyl, phenethyl, lower alkanoyl of from 1–5 carbon atoms such as formyl, acetyl or trifluoroacetyl, lower alkyl of 1–5 carbon atoms especially methyl, lower alkenyl of 3–5 carbon atoms such as allyl or dimethylallyl, propargyl or phenacyl;

$R_2$ and $R_3$ are each hydrogen, lower alkyl of 1–5 carbon atoms especially methyl, lower alkanoyl of 2–5 carbon atoms especially acetyl, benzyl or, when taken together, methylene; and $R_4$ is hydrogen or one or two substituents such as trifluoromethyl, halo such as chloro, bromo or fluoro, methyl, methoxy, acetoxy, methylthio or especially hydroxy.

$R_2$ and $R_3$ are preferably hydrogen for maximal dopaminergic activity. The O-acyl derivatives are useful for oral activity. For convenience sake, the most useful O-acyl derivatives are those in which all phenolic hydroxyl groups are in esterified form with identical acyl groups. For intermediate use, $R_2$ and $R_3$ are preferably methyl or benzyl. Prime blocking groups at position 3 are trifluoroacetyl and formyl but others such as benzyl, phenethyl, lower alkanoyl, furoyl, thenoyl or phenacyl may be used in intermediate compounds.

Among the compounds of this invention represented by the structural Formula I above which have primary utility in their biological activity in screening tests described hereafter, are those in which:

R and $R_4$ are as described for Formula I;

$R_1$ is hydrogen, lower alkyl of 1–5 carbons or lower alkenyl of 3–5 carbons; and $R_2$ and $R_3$ are hydrogen or lower alkanoyl of 2–5 carbons.

Another group of compounds within those of Formula I which has primary utility as chemical intermediates as described hereafter are those in which:

R, $R_2$ or $R_3$ are as described for Formula I; and $R_1$ is benzyl, phenethyl, lower alkanoyl of from 1–5 carbons or phenacyl or, when $R_2$ and $R_3$ are other than hydrogen or alkanoyl, hydrogen.

It should be made clear that there is not a distinct line of demarcation between these two subgroups. Certain compounds of the first group may be of utility as intermediates; while many, if not all, of the compounds of the second group will have some degree of biological activity. For example 6-methyl-7,8-dimethoxy-1-(p-methoxyphenyl)-2,3,4,5-tetrahydro-1H-3-benzazepine as the hydrochloride at 300 mcg/kg i.v. in three normotensive dogs increased renal blood flow 24.5% and decreased renal vascular resistance 15.2% demonstrating an antihypertensive activity even though its primary use is described hereafter as an intermediate.

A subgeneric group of compounds having dopaminergic activity within the above illustrative generic group are those of Formula I in which:

R is propyl or methyl;

$R_1$ is hydrogen, allyl, ethyl or methyl;

$R_2$ and $R_3$ are the same and are hydrogen, isobutyryl or acetyl; and $R_4$ is hydrogen, p-hydroxy, p-acetoxy or p-isobutyryloxy.

Individual compounds having exceptional dopaminergic activity are the following:

7,8-dihydroxy-3,6-dimethyl-1-phenyl-2,3,4,5-tetrahydro-1H-3-benzazepine;

7,8-dihydroxy-6-n-propyl-1-phenyl-2,3,4,5-tetrahydro-1H-3-benzazepine;

7,8-dihydroxy-6-methyl-1-(p-hydroxyphenyl)-2,3,4,5-tetrahydro-1H-3-benzazepine;

7,8-dihydroxy-6-n-propyl-1-(p-hydroxyphenyl)-2,3,4,5-tetrahydro-1H-3-benzazepine; and their nontoxic salts.

The compounds in which the 7,8-dihydroxy groups are blocked by O-protective groups such as the methoxy, benzyloxy or methylenedioxy-containing compounds as well as the compounds having the N-blocking groups mentioned are as stated above of primary interest as intermediates. The 6-methyl and 6-propyl containing compounds are particularly active dopaminergic compounds, the former especially so with a 3-methyl substituent or a 1-(p-hydroxyphenyl) substituent.

The addition salts which are acceptable as nontoxic for pharmaceutical purposes or in general for synthetic purposes but which have the utility of the corresponding free bases of formula I are included in this invention. These salts are prepared by methods well known to the art and may be formed with both inorganic or organic acids, for example: maleic, fumaric, benzoic, ascorbic, pamoic, succinic, bismethylenesalicyclic, methanesulfonic, ethanedisulfonic, acetic, oxalic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids. The nontoxic hydrohalic acid salts are preferred but the methanesulfonic acid salts are useful for their stability, solubility and oral absorption.

Similarly the quaternary salts include those prepared from organic halides such as methyl iodide, ethyl iodide, benzyl chloride and the like as known to the art.

It will be obvious to one skilled in the art that the compounds of Formula I may be present as diastereoisomers which may be resolved into d and l optical isomers. Resolution of the optical isomers may be conveniently accomplished by fractional crystallization of their salts with optically active acids from appropriate solvents. Such methods are described in Swiss Patent No. 555,831. Unless otherwise specified herein or in the claims, it is intended to include all isomers, whether separated or mixtures thereof. Where isomers are separated, the desired pharmacological activity will usually predominate in one of the isomers.

The compounds of this invention are prepared by reacting the 6-lithium intermediates which are prepared from the 6-bromo congeners with carbon dioxide to form the intermediate 6-carboxy-1-phenyl-2,3,4,5-tetrahydro-1H-3-benzazepines or subsequently its ester or with a formylating agent such as N-methylformanilide or another tertiary formamide to prepare the intermediate 6-formyl-1-phenyl-2,3,4,5-tetrahydro-1H-3-benzazepines. Any chemical centers of the structures which may be reactive under the conditions for forming a 6-metal benzazepine and reacting it with carbon dioxide or a formylating agent should be protected as known to the art such as by forming the ether derivatives of hydroxy substituents or, at reactive N-hydrogen centers such as at 3, acyl formation.

The 6-carboalkoxy intermediates are reacted with a lower alkyl lithium agent to give the 6-lower alkanoyl compounds of Structure II below:

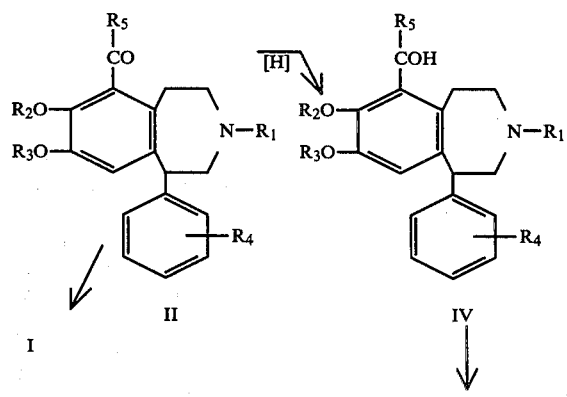

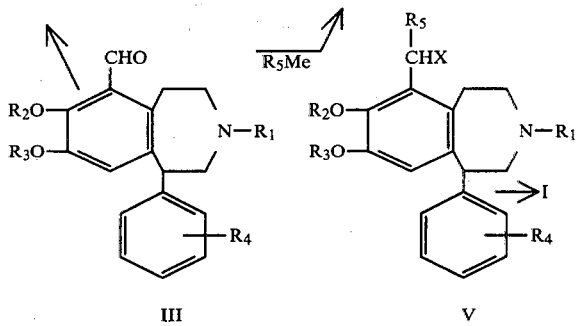

in which:

$R_5$ is lower alkyl of one less carbon atom than R of Formula I;

X is chloro or bromo;

Me is a reactive alkali metal such as sodium, potassium or lithium or magnesium halide (a Grignard reagent);

$R_1$–$R_4$ are moieties as defined above for Formula I protected from the various reaction conditions as explained above and as illustrated in the examples.

The 6-lower alkanoyl substituted compounds of Formula II may be reduced directly to the 6-lower alkyl containing compounds of this invention by using conventional reducing agents such as a Clemmensen or Wolff-Kischner reduction. Preferably the compounds of Formula II are reduced to the corresponding α-hydroxy lower alkyl compounds of Formula IV using an alkali metal borohydride, trimethoxyborohydride, lithium aluminum hydride or catalytic hydrogenation such as using nickle, platinum or palladium catalysts.

The 6-formyl benzazepines (III) are optionally reacted with a lower alkyl alkali metal such as methyl or ethyl lithium or a Grignard reagent ($R_5$Me) to give the same 6-α-hydroxy lower alkyl benzazepine produced from the 6-carbalkoxy intermediates. These compounds (IV) are converted to the desired 6-lower alkyl benzazepines of Formula I by any known chemical reduction but preferably via the 6-α-haloalkyl intermediate (V). The latter compounds are easily prepared by treatment of the compounds of Formula IV with concentrated mineral acid such as hydrochloric or hydrobromic acid. The halo atom is removed such as by use of an alkali metal borohydride or trimethoxyborohydride to give the end products of this invention after optional removal of protective groups such as by acid, alkali or hydrogenation treatment and then optional formation of the desired salt form.

Among the new compounds useful as chemical intermediates in the reaction scheme described above for the preparation of the 6-alkyl-7,8-dihydroxy-3-benzazepine end products of this invention are those of the Formula VI.

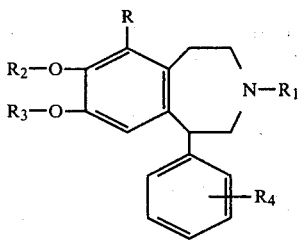

in which:

R is an α-hydroxy or α-chloroalkyl of 1–6 carbons;

$R_1$ is hydrogen, formyl or methyl;

$R_2$ and $R_3$ are methyl, benzyl or, when taken together, methylene; and $R_4$ is hydrogen or one or two substituents from the group comprising trifluoromethyl, halo, methyl, methylthio or methoxy; or nontoxic chemically stable acid addition salts thereof.

To prepare the compounds of Formula I where $R_1$ is lower alkyl or akenyl, phenacyl, propargyl, phenethyl, benzyl, etc., the corresponding benzazepines wherein $R_1$ is hydrogen may be N-alkylated or N-acylated by standard methods with a reactive lower alkyl ester such as the bromide or chloride, a reactive alkenyl halide such as allyl bromide or chloride or, in certain cases as known to the art, by N-acylation followed by amide reduction. The latter is used to prepare 3-furylmethyl and thienylmethyl derivatives. Advantageously, to obtain the preferred products where $R_2$ and/or $R_3$ are hydrogen the reaction with the alkylating agent is carried out on the corresponding methoxy substituted benzazepines in an inert solvent such as methanol or acetone, preferably at reflux temperature and in the presence of a basic condensing agent such as potassium hydroxide or carbonate. Treatment of the resulting product for example, with boron tribromide or other ether splitting agents, gives the active hydroxy substituted benzazepines.

Direct N-alkanoylation of the dihydroxy compounds may be possible under controlled conditions as known to the art. Any undesirable O-acylation may necessitate a mild hydrolysis treatment.

The important compounds of Formula I where $R_1$ is methyl are conveniently prepared from methoxy substituted benzazepines wherein $R_1$ is hydrogen by a reductive formylation reaction with formic acid/formaldehyde. Treatment of the resulting product with boron tribromide gives once again the corresponding 7,8-dihydroxy-3-methyl substituted benzazepines.

To prepare the compounds of Formula I in which $R_2$ or $R_3$ is alkanoyl whenever there are no interfering substituents, the corresponding 3-benzyl-7,8-dihydroxy-3-benzazepine (obtained by N-alkylation of the hydroxy-benzazepine with benzyl bromide in the presence of potassium carbonate) is treated with the appropriate alkanoic acid anhydride or chloride, for example acetic anhydride, and the resulting alkanoyloxy substituted benzazepine is then hydrogenated in the presence of palladium-on-carbon to remove the protective benzyl group. The dialkanoyloxy derivatives such as the important 7,8-diacetoxy compounds can also be prepared by direct O-acylation of the 6-lower alkyl-7,8-dihydroxy-1-phenyl-2,3,4,5-tetrahydro-1H-3-benzazepine hydrobromide in trifluoroacetic acid at ambient temperature with the anhydride or halide. The N or 3-lower alkanoyl congeners in the dihydroxy series may be prepared conveniently by N-acylating the methylenedioxy derivative followed by splitting the protective group.

The benzazepine compounds of Formula I especially those in which R is methyl or propyl and $R_1$ is methyl or allyl have antiparkinsonism activity due to central dopaminergic activity as demonstrated by employing a modified standard animal pharmacological test procedure reported by Ungerstedt et al., in *Brain Research* 24, 1970, 485–493. This activity in the compounds of Formula I which have biological activity may in certain cases be more pronounced than the peripheral or cardiovascular activity. This test procedure is based on a drug induced rotation of rats having extensive unilateral lesions of the substantia nigra. Briefly, the test comprises the quantitative recording of rotational behavior in rats in which 6-hydroxydopamine lesions of the nigrostriatal dopamine system have been produced.

A unilateral brain lesion in the left substantia nigra causes the dopamine receptor in the left caudate to become hypersensitive following the resulting degeneration of the nigral cell bodies. These lesions destroy the source of the neurotransmitter dopamine in the caudate but leave the caudate cell bodies and their dopamine receptors intact. Activation of these receptors by drugs which produce contralateral rotation, with respect to the lesioned side of the brain, is used as a measure of central dopaminergic activity of the drug.

Compounds which are known to be clinically effective in controlling parkinsonism, such as, for example, L-dopa and apomorphine, are also effective in this rat turning model. These compounds directly activate the dopamine receptors and cause contralateral rotation of the lesioned rat.

Rotational activity is defined as the ability of a compound to produce 500 contralateral rotations during a two-hour period after administration, usually intraperitoneally. The dose corresponding to 500 contralateral rotations per two hours is obtained and assigned as the $RD_{500}$ value. For example the preferred 3,6-dimethyl-7,8-dihydroxy-1-phenyl-2,3,4,5-tetrahydro-1H-3-benzazepine hydrobromide had an $RD_{500}$ (i.p.) of 0.05 mg/kg; $RD_{1000}$ (8.0) 5.66 mg/kg. 6-Methyl-7,8-dihydroxy-1-phenyl-2,3,4,5-tetrahydro-1H-3-benzazepine hydrobromide is less active, $RD_{500}=0.96$ mg/kg. 7,8-Dihydroxy-6-methyl-1-(p-hydroxyphenyl)-2,3,4,5-tetrahydro-1H-3-benzazepine hydrobromide at 10 mg/kg (i.p.) induced $99\pm 33$ rotations.

The peripheral or cardiovascular dopaminergic activity of the compounds of this invention is demonstrated using the methods of testing described in the U.S. Pat. No. 4,011,319. For example 6-n-propyl-7,8-dihydroxy-1-phenyl-2,3,4,5-tetrahydro-1H-3-benzazepine hydrobromide had an $ED_{15}$ (i.v.) of 0.57 mcg/kg in the anesthetized dog compared to dopamine's 2.7 mcg/kg value in decreasing renal vascular resistance. The desmethyl congener had an $ED_{15}$ of 3 mcg/kg in the same test. 6-n-Propyl-7,8-dihydroxy-(1-p-hydroxyphenyl)-2,3,4,5-tetrahydro-1H-3-benzazepine hydrobromide had an $ED_{50}$ of 101 mcg/kg. 7,8-Dihydroxy-6-methyl-1-(p-hydroxyphenyl)-2,3,4,5-tetrahydro-1H-3-benzazepine hydrobromide has an $ED_{15}$ (i.v.) of 2.8 mcg/kg but has a high biological selectivity factor. Certain other 6-lower alkyl congeners of this series of this invention had relatively lower peripheral dopaminergic activity such as the 6-methyl or 6-ethyl congeners. Also a number of the series may have substantial central and diminished peripheral dopaminergic activity or vice versa. This may be due more to the distribution of the compound to the active sites of action rather than lack of inherant dopaminergic activity.

The pharmaceutical compositions of the invention containing a compound of Formula I which has dopaminergic activity are prepared in conventional dosage unit forms by incorporating the chemical compound or a pharmaceutically carrier according to accepted procedures in a nontoxic amount sufficient to produce the desired pharmacodynamic activity in a subject, animal or human. Preferably the compositions will contain the active ingredient in an active but nontoxic amount selected from about 50 mg to about 1000 mg of active ingredient per dosage unit but this quantity depends on the specific type and potency of biological activity possessed by the individual compounds as well as the conditions of patient and route of administration.

The pharmaceutical carrier employed may be, for example, either a solid or liquid. Exemplary of solid carriers are lactose, terra alba, sucrose, talc, gelatin, agar, pectin, acacia, magnesium stearate, stearic acid, and the like. Exemplary of liquid carriers are syrup, peanut oil, olive oil, water and the like. Similarly the carrier or diluent may include any time delay material well known to the art, such as glyceryl monostearate or glyceryl distearate alone or with a wax.

A side variety of pharmaceutical forms can be employed. Thus, if a solid carrier for oral administration is used the preparation can be tableted, placed in a hard gelatin capsule in powder or pellet form, or in the form of a trouche or lozenge. The amount of solid carrier will vary widely but preferably will be from about 25 mg to about 1 g. If a liquid carrier is used, the preparation will be in the form of a syrup, emulsion, soft gelatin capsule, sterile injectable liquid such as an ampul, or an aqueous or nonaqueous liquid suspension.

The pharmaceutical preparations are made following the conventional techniques of the pharmaceutical chemist involving mixing, granulating and compressing when necessary, or variously mixing and dissolving the ingredients as appropriate to give the desired end product.

The method of producing dopaminergic activity in accordance with this invention comprises administering internally to a subject in need of such activity a compound of Formula I or a pharmaceutically acceptable acid addition salt thereof, usually combined with a pharmaceutical carrier, in a nontoxic amount sufficient to produce said activity as described above. The route of administration may be any route which effectively transports the active compound to the dopamine receptors which are to be stimulated such as orally or parenterally, the oral route being preferred. Advantageously, equal doses will be administered several times such as two or three times a day with the daily dosage regimen being selected from about 100 mg to about 2 g. When the method described above is carried out antiparkinsonism and/or hypotensive activity is produced with a minimum of side effects.

The terms "lower alkyl", "lower alkoxy", "lower alkanoyl" and such alone or combined are used to mean chemically stable straight or branched aliphatic groups having up to 6 carbon atoms unless otherwise noted.

The following examples are designed solely to illustrate the preparation and use of the compounds of this invention. The temperatures are Centigrade. Other variations of these examples will be obvious to those skilled in the art.

EXAMPLE 1

A. 7,8-Dimethoxy-1-phenyl-2,3,4,5-tetrahydro-1H-3-benzazepine (280 g, 0.75 mole) was dissolved in 1700 ml of acetic acid. Bromine (280 g, 1.75 mole) was added in a thin stream. This reaction was stirred for two hours. The precipitate, which formed after 1 hour, was collected and washed with ether. It was dissolved in boiling methanol and acetone was added to destroy the bromine excess. 6-Bromo-7,8-dimethoxy-1-phenyl-2,3,4,5-tetrahydro-1H-3-benzazepine hydrobromide was allowed to crystallize from the methanol and a second crop was obtained by adding ether to the mother liquor. Yield 298 g, 77% m.p. 236°–238°. This bromination may be applied to any suitably O- and N-protected 7,8-dialkoxy or alkanoyloxybenzazepine having a free 6-position in which the substituted 1-phenyl ring is not more reactive to halogenation than is the 6-position of the nucleus.

B. Isovanillin (76.1 g, 0.5 m) was suspended in 750 ml of chloroform. Bromine (27.3 ml, 0.5 m) in 200 ml of chloroform was added at 0° slowly. Water was added to give the desired 2-bromo-3-hydroxy-4-methoxy-benzaldehyde, m.p. 197°–203°.

The aldehyde product (46.2 g, 0.2 mole) was dissolved in 300 ml of dry dimethylformamide, 69.1 g of potassium carbonate was added. 28.4 ml (0.30 mole) of dimethylsulfate was added at room temperature dropwise. After the addition the reaction was heated on the steam bath for 10 minutes. 29 ml of water was added dropwise and the reaction again heated for 5 minutes on the steam bath. The reaction was then poured into ice water and the precipitate collected, 2-bromo-3,4-dimethoxybenzaldehyde, m.p. 80°–81.5°.

The dimethoxybenzaldehyde (10 g, 0.04 mole) was dissolved in 100 ml of ethanol 5 g (0.132 mole) of sodium borohydride was added. The reaction was stirred for 1 hour. The reaction mixture was poured into water and extracted into methylene chloride to give the benzyl alcohol (m.p. 74°–76.5°). This was converted to the benzyl chloride as a tan liquid, using benzene and conc. hydrochloric acid then to the benzyl cyanide, m.p. 48°–55° using sodium cyanide in dimethylsulfoxide.

The benzyl cyanide (8.05 g, 0.315 mole) was dissolved in 80 ml of dry tetrahydrofuran and then added slowly to 80 ml of 1 M diborane in tetrahydrofuran at 5°. After refluxing for 2 hours, the mixture was cooled and 40 ml of methanol added carefully. After refluxing shortly and standing overnight the mixture was concentrated to give a tan oil. Dilute hydrochloric acid was added. The material was washed with ether, filtered and the filtrate made basic with 40% sodium hydroxide. After extracting with ether, washing, drying and evaporated the extracts the desired phenethylamine was obtained as a viscous, light yellow oil.

The phenethylamine (0.12 mole) is heated to 115° in an oil bath. Styrene oxide (14.4 g 0.12 mole) is added and the reaction heated for 1 hour. After cooling to N30°, 2:1 petroleum ether/acetone is added to give (N-[(2-hydroxy-2-phenylethyl)]-N-[2-(2'-bromo-3'-4'-dimethoxyphenyl)ethyl]amine.

The hydroxyphenethylamine (0.0445 mole) is dissolved in 60 ml of trifluoroacetic acid and 4.05 ml of concentrated sulfuric acid is added. The reaction is refluxed for 2 hours. After cooling most of the trifluoroacetic acid is stripped off and the residue is poured into water. It is made basic with 10% sodium hydroxide and extracted with ether twice. The ether is dried and evaporated to give 6-bromo-7,8-dimethoxy-1-phenyl-2,3,4,5-tetrahydro-1H-3-benzazepine.

Using this general procedure with variously substituted styrene oxides having one or more methyl, methoxy, methylthio, trifluoromethyl groups gives the corresponding 6-bromo intermediates not readily prepared by direct bromination which are used for preparing the 6-alkyl derived compounds of this invention by the methods described hereafter.

The 6-bromo-7,8-dimethoxy compound (100 g) in a large excess of ethyl formate is heated at reflux for 10 hours. Evaporation in vacuo and purification by fractional recrystallization gives the 3- or N-formyl derivative.

6-Bromo-3-formyl-7,8-dimethoxy-1-phenyl-2,3,4,5-tetrahydro-1H-3-benzazepine (82.6 g, 0.212 mole) was dissolved in 1500 ml of toluene and added to a mixture of 0.678 mole of n-butyl lithium, 251 ml of toluene and 250 ml of ether at −78°. After addition, the mixture was stirred for 10 minutes. N-Methylformanilide (86 g, 0.636 mole) was added to the mixture followed by stirring at −78° for 1 hour. The cooling bath was removed and 500 ml of 10% hydrochloric acid and 250 ml of water were added to give the 6-formyl derivative as the hydrochloride salt, m.p. 209°–210°, after standing overnight. This material as the free base N-formylated in an excess of ethyl formate at reflux for 6 hours.

The 3,6-diformyl-7,8-dimethoxy product was reacted with a slight excess of ethyl lithium in ethyl ether at 0°–5° to give 7,8-dimethoxy-6-α-hydroxypropyl-1-phenyl-2,3,4,5-tetrahydro-1H-3-benzazepine. Alternatively ethyl magnesium bromide can be used with the 3-desformyl compound.

A mixture of 7.5 g of 7,8-dimethoxy-6-α-hydroxypropyl-1-phenyl-2,3,4,5-tetrahydro-1H-3-benzazepine in 500 ml of ethylformate was heated at reflux for 5 hours then worked up using medium pressure liquid chromatography to give the N-formyl derivative.

This material (4.9 g) in 150 ml of chloroform and 50 ml of concentrated hydrochloric acid was heated at reflux for 2 hours. A small amount of aldehyde by-product was removed by bisulfite extraction to give the 6-α-chloropropyl compound.

This material (3.6 g) in dry dimethylsulfoxide was added dropwise to a solution of 1.07 (0.028 mole of sodium borohydride in dry dimethyl sulfoxide. After stirring at room temperature the mixture was heated on the steam bath for several hours then poured into water. The product was taken into ethyl ether-ethyl acetate and purified by chromatography using methanol-chloroform to give 3-formyl-7,8-dimethoxy-6-propyl-1-phenyl-2,3,4,5-tetrahydro-1H-3-benzazepine.

This material (1.9 g, 0.0054 mole) in 50 ml of ethanol and 10 ml of 40% sodium hydroxide was heated at reflux for 2 hours. After stripping, the residue was taken up in methylene chloride-water. The combined organic layers were dried and evaporated to give the 7,8-dimethoxy compound which (1 g) was reacted with 1 ml of boron tribromide in dry methylene chloride for 3 hours. After stripping and cooling the residue was treated with methanol. The methanol was taken off and the residue dissolved in hot water (20 ml). Evaporation and cooling gave the dopaminergic agent 7,8-dihydroxy-6-n-propyl-1-phenyl-2,3,4,5-tetrahydro-1H-3-benzazepine hydrobromide, m.p. 226°–229° (dec.). The base is regenerated with treatment of bicarbonate methylene chloride. The methanesulfonate salt is prepared from the base using methane sulfonic acid.

EXAMPLE 2

A. A mixture of 25 g (0.068 mole) of 6-bromo-7,8-dimethoxy-1-phenyl-2,3,4,5-tetrahydro-1H-3-benzazepine in a minimum amount of toluene diluted with ethyl ether under dry, degassed conditions was reacted with 100 ml (0.24 mole) of n-butyl lithium in 100 ml of ethyl ether at −78°.

After a few minutes, the mixture was poured onto a slurry of dry ice (carbon dioxide). The ether slurry was extracted with ether, then acidified with dilute hydrochloric acid and warmed on the steam bath briefly. The acid layer was extracted with ether then stripped to leave a solid product, 6-carboxy-7,8-dimethoxy-1-phenyl-2,3,4,5-tetrahydro-1H-3-benzazepine hydrochloride, m.p. 225°–226° (dec.). More product, m.p. 230°–235°, was obtained from the mother liquor by the use of sodium bicarbonate, ethyl acetate extraction and acidification with hydrochloric acid.

The 6-carboxy compound (3.0 g) was dissolved in methylene chloride and reacted with an excess of trifluoro acetic anhydride. After stirring for one hour, the mixture was cooled to 0° and an excess of methanol added. The volatiles were stripped. The residue was taken up in methylene chloride, washed with hydrochloric acid, then sodium bicarbonate solution. The organic layer was dried and evaporated to give the 3-trifluoroacetyl compound.

A mixture of 9.5 g (0.021 mole) of 6-carbomethoxy-7,8-dimethoxy-1-phenyl-3-trifluoroacetyl-2,3,4,5-tetrahydro-1H-3-benzazepine in dry toluene was reacted with 39 ml of methyl lithium in 100 ml of dry ethyl ether at 0° for one hour after dropwise addition.

The reaction was worked up by adding an excess of 10% hydrochloric acid and allowing it to stand at room temperature overnight. The non-organic layer and precipitate were collected, made basic with alkali and extracted by ethyl acetate. The toluene reaction mixture was taken through the salt isolation. The combined product as the base was dissolved in ether, made acid with ethereal hydrogen chloride to form the hydrochloride salt and purified by recrystallization from methanol-ethyl acetate to give 6-acetyl-7,8-dimethoxy-1-phenyl-2,3,4,5-tetrahydro-1H-3-benzazepine hydrochloride, m.p. 235°–236°.

B. A mixture of 4 g (0.1 mole) of 6-carboxy-7,8-dihydroxy-3-trifluoroacetyl-1-phenyl-2,3,4,5-tetrahydro-1H-3-benzazepine, prepared by boron tribromide treatment of the 7,8-dimethoxy congener, in 50 ml of dry dimethylformamide was reacted with 0., 35 ml of benzyl chloride and 8.4 g of potassium carbonate at 160°–175°. The mixture was poured onto ice and taken through ether to give 93% of the desired dibenzyl ether benzyl ester.

This material, 6.2 g, was reacted with methyl lithium in ethyl ether at 0° as described above to give the 6-acetyl-7,8-dibenzyloxy-1-phenyl-2,3,4,5-tetrahydro-1H-3-benzazepine, m.p. 229°–233°.

The 6-acetyl compound above is reduced with sodium borohydride to give the 6-α-hydroxyethyl compound which is then reacted with concentrated hydrochloric acid and sodium borohydride as described in Example 1 to give the 7,8-dimethoxy-6-ethyl-1-phenyl-2,3,4,5-tetrahydro-1H-3-benzazepine base and its hydrochloride and methyl sulfonate salts.

The dibenzyloxy intermediate from B above can also be used to prepare 7,8-dibenzoxyl-6-ethyl-phenyl-2,3,4,5-tetrahydro-1H-3-benzazepine. The protective O-benzyl groups are removed by hydrogenation in acidic aqueous ethyl acetate using 10% palladium-on-charcoal at 60° to give 7,8-dihydroxy-6-ethyl-1-phenyl-2,3,4,5-tetrahydro-1H-3-benzazepine as its base, hydrochloride or methane sulfonate.

Alternatively the dibenzyl intermediate is N-methylated by heating at reflux in formic acid-ethyl formate mixture to give, after dibenzylation, 6-ethyl-7,8-dihydroxy-3-methyl-1-phenyl-2,3,4,5-tetrahydro-1H-3-benzazepine hydrobromide hydrate, m.p. 160° (dec.).

EXAMPLE 3

In a dry flask containing 10 mmole of piperonal cyclohexylimine was placed 75 ml of dry tetrahydrofuran. The mixture cooled to −78°, and 10.5 mmole of butyl lithium in hexane was added over a 5 minute period. This was stirred for 15 minutes at −78°, and then a solution of 15 mmole of hexabromoethane in dry tetrahydrofuran added dropwise. Tetrabromomethane may also be used. This was stirred for 15 minutes, warmed to room temperature, and poured into water. This was extracted with methylene chloride, which was evaporated under vacuum and hydrolyzed by 10% aqueous hydrochloric acid to give 2-bromopiperonal. Reference: F. E. Ziegler and K. W. Fowler, J.O.C. 41 1564 (1976). This product is reduced with sodium borohydride, reacted with sodium cyanide and the resulting phenylacetonitrile reduced with borane to give the phenethylamine. This compound is condensed with m-methoxystyrene oxide to give the α-hydroxy-phenethylamine intermediate which is reacted with an excess of trifluoroacetic acid at room temperature for 18 hours to give 6-bromo-7,8-methylenedioxy-1-(m-methoxyphenyl)-2,3,4,5-tetrahydro-1H-3-benzazepine.

This material after N-formylation is treated with butyl lithium in toluene-ether and the N-methylformanilide to give the 6-formyl. This intermediate is converted using butyl magnesium bromide as described above to 6-amyl-7,8-dihydroxy-1-(m-methoxyphenyl)-2,3,4,5-tetrahydro-1H-3-benzazepine and by selective hydrolysis using boron trichloride or borontribromide respectively.

EXAMPLE 4

A. 6-Bromo-3-formyl-7,8-dimethoxy-1-(p-methoxyphenyl)-2,3,4,5-tetrahydro-1H-3-benzazepine (15.4 g from N-formylation of starting material prepared as in Example 1 using methylformate) was reacted with 53 ml of n-butyl lithium in 400 ml of toluene-300 ml of ether at −78° then with N-methylformanilide as described to give 6-formyl-7,8-dimethoxy-1-(p-methoxyphenyl)-2,3,4,5-tetrahydro-1H-3-benzazepine hydrochloride, m.p. 131°–136°.

B. A mixture of 10 g (0.0255 mole) of 6-bromo-7,8-dimethoxy-1-(p-methoxyphenyl)-2,3,4,5-tetrahydro-1H-3-benzazepine and 42 ml of n-butyl lithium was reacted to give the 6-lithium derivative which is reacted with dry ice in excess as described above to give 6-carboxy-7,8-dimethoxy-1-(p-methoxyphenyl)-2,3,4,5-tetrahydro-1H-3-benzazepine hydrochloride, m.p. 242°–245° (dec.). This compound is esterified in n-butanolhydrogen chloride to give the 6-carbobutoxy compound.

Either the 6-formyl or the 6-carbobutoxy intermediates from above are converted into 6-propyl-7,8-dihydroxy-1-(p-hydroxyphenyl)-2,3,4,5-tetrahydro-1H-3-benzazepine base or its hydrochloride or methane sulfonate salts by the methods of Examples 1 or 2.

EXAMPLE 5

A mixture of 4.0 g (0.011 mole) of the 6-chloromethyl-N-formyl compound prepared from the 6-hydroxymethyl congener described hereafter using conc. hydrochloric acid in 50 ml of dry chloroform was added to a mixture of 0.82 g (0.022 mole) of sodium borohydride in 50 ml of dimethylsulfoxide. After stirring at room temperature overnight, the reaction mixture was poured into cold hydrochloric acid. The aqueous layer was extracted with ethyl ether twice. The ethereal layers were washed with water, dried and evaporated to give, by nuclear magnetic resonance and thin layer chromatography analysis, a mixture of a small amount of 3,6-dimethyl congener with 3-formyl-6-methyl compound.

The mixture was dissolved in 50 ml of tetrahydrofuran and added to a mixture of 50 ml of tetrahydrofuran and 20 ml of 1 M. Borane in tetrahydrofuran at 0°. After stirring for 1 hour at 0°, the mixture is allowed to warm to room temperature overnight. Hydrochloric acid (6 N) was added dropwise to the mixture until the evolution of hydrogen ceased. Hydrochloric acid (12 N) (10 ml) was added and the organic solvent stripped off. The residue was taken up in ether and water. The dried ethereal extracts were evaporated. The residue was dissolved in 50 ml of methanol and 20 ml of ethereal hydrogen chloride. The mixture was heated at reflux for 2 hours; the methanol stripped to give 3,6-dimethyl-7,8-dimethoxy-1-phenyl-2,3,4,5-tetrahydro-1H-3-benzazepine hydrochloride, m.p. 252°–254°. Total yield, including like material recovered from the aqueous layer was 59%.

The dimethoxyhydrochloride (2.19 g, 0.0071 mole) was treated with aqueous sodium hydroxide in methylene chloride solution. The organic soluble material was removed, dried, filtered and cooled to −15° at which time 3 ml of boron tribromide was added. After stirring at room temperature for 4 hours, the volatiles were stripped. The residue was cooled to −15° and dissolved in methanol. After stripping, the residue was recrystallized twice from water to give 3,6-dimethyl-7,8-dihydroxy-1-phenyl-2,3,4,5-tetrahydro-1H-3-benzazepine hydrobromide; m.p. 168°–170°. The base is regenerated in bicarbonate-ether mixture. The methane sulfonate salt is prepared by shaking the base in ether with an excess of methane sulfonic acid.

The 3,6-dimethyl compound as its hydrochloride salt at 7 mg/kg, p.o. exhibited rotational activity in the central dopaminergic test described above with a duration of four hours.

EXAMPLE 6

A mixture of 4.5 g of 6-propyl-7,8-dimethoxy-1-phenyl-2,3,4,5-tetrahydro-1H-3-benzazepine, 0.02 mole of n-butyl bromide and 0.02 mole of potassium hydroxide is dissolved in 120 ml of dry methanol and refluxed for 48 hours. The reaction mixture is evaporated to dryness, taken up in ethyl acetate and filtered to remove inorganic salts. The filtrate is washed with water, dried and evaporated to give 3-n-butyl-6-propyl-7,8-dimethoxy-1-phenyl-2,3,4,5-tetrahydro-1H-3-benzazepine.

The 3-n-butylbenzazepine (0.01 mole) is dissolved in 120 ml of dry methylene chloride and 0.032 mole of boron tribromide is added dropwise at −10° C. The solution is warmed to room temperature and stirred for two hours. The excess boron tribromide is destroyed with methanol added dropwise with ice-cooling. The cold solution is refluxed on the steam bath to remove hydrogen bromide and trimethylborate and then evaporated to yield 3-n-butyl-6-propyl-7,8-dihydroxy-1-phenyl-2,3,4,5-tetrahydro-1H-3-benzazepine hydrobromide. Other N-alkyl derivatives especially the 3-ethyl compound are made similarly.

EXAMPLE 7

A 4.0 g sample of 3-benzyl-6-propyl-7,8-dihydroxy-1-phenyl-2,3,4,5-tetrahydro-1H-3-benzazepine (prepared from the 3-unsubstituted benzazepine by reaction with benzyl bromide in the presence of potassium carbonate) is dissolved in 50 ml of acetic anhydride and the solution is heated on a steam bath for one hour. The reaction mixture is cooled, ice-water is added and the solution is evaporated to dryness. The residue is triturated with ethyl acetate, the solution washed with water, dried and the solvent removed in vacuo to leave an oil. The latter is dissolved in ether and ethereal hydrogen chloride is added to precipitate 3-benzyl-6-propyl-7,8-diacetoxy-1-phenyl-2,3,4,5-tetrahydro-1H-3-benzazepine hydrochloride.

The diacetoxy compound prepared above, 3.5 g, is dissolved in 100 ml of ethanol and 1 g of 10% palladium-on-carbon is added. The mixture is hydrogenated in a Parr apparatus at 50° under 50 psi of hydrogen for one hour. The reaction mixture is filtered and the filtrate is evaporated to give 6-propyl-7,8-diacetoxy-1-phenyl-2,3,4,5-tetrahydro-1H-3-benzazepine hydrochloride.

Alternatively 6-propyl-7,8-dihydroxy-1-phenyl-2,3,4,5-tetrahydro-1H-3-benzazepine hydrobromide (10 g) is dissolved in trifluoroacetic acid and reacted with a stoichiometric amount of acetyl bromide at room temperature. The next day the reaction mixture is evaporated and the residue recrystallized to give the desired diacetoxy derivative.

EXAMPLE 8

6-Formyl-7,8-dimethoxy-1-phenyl-2,3,4,5-tetrahydro-1H-3-benzazepine hydrochloride (6.3 g, 0.018 mole) was converted to the free base by aqueous alkali and methylene chloride. The organic layer was dried with magnesium sulfate and evaporated. The residue was refluxed in 500 ml of ethyl formate for 2 hours. The excess formate was distilled off and the residue was dissolved in ethyl acetate and extracted once with dil. hydrochloric acid. Drying and evaporating left 3,6-diformyl-7,8-dimethoxy-1-phenyl-2,3,4,5-tetrahydro-1H-3-benzazepine.

This compound (6.1 g, 0.018 mole) was dissolved in 50 ml of isopropanol. Solid sodium borohydride was added slowly until 1.33 g (0.036 mole) had been added. The reaction stirred at room temperature for 2 hours, then worked up by the careful addition of water, then dil. hydrochloric acid to the cooled solution. When the solution was acidic, the isopropanol was stripped off. Water and ether were added to the residue to dissolve it. The ethereal layer was washed with bicarbonate, dried and evaporated to give an oily 3-formyl-7,8-dimethoxy-6-hydroxymethyl-1-phenyl-2,3,4,5-tetrahydro-1H-3-benzazepine.

The 6-hydroxymethyl compound (4.1 g, 0.012 mole) was dissolved in 75 ml of chloroform and 10 ml of conc. hydrochloric acid was added. The mixture was stirred vigorously and heated at reflux for 1 hour. After separation of the chloroform, the aqueous layer was extracted with chloroform. The dried chloroform solution was evaporated to give 6-chloromethyl-3-formyl-7,8-dimethoxy-1-phenyl-2,3,4,5-tetrahydro-1H-3-benzazepine as an oil.

This 6-chloromethyl compound (4.0 g, 0.011 mole) was dissolved in 40 ml of dry dimethylsulfoxide then added dropwise to a mixture of 0.83 g (0.022 mole) of sodium borohydride in 40 ml of dry dimethylsulfoxide. The reaction mixture was stirred for 2.5 hours at room temperature, then was poured into water. Concentrated hydrochloric acid was added until the evolution of hydrogen ceased and the solution was acidic. The aqueous solution was extracted twice with ether. The ethereal extracts were washed with water, dried and evaporated to give the 6-methyl-3-amide as an oil.

The oil (~4 g) was dissolved in 50 ml of ethanol and 10 ml of 40% sodium hydroxide was added. The reaction was heated at reflux for 1½ hours. The ethanol was stripped off and the residue dissolved in ether and water. The ether layer was washed again with water and dried. The solution was acidified with ethereal hydrogen chloride. The solid was separated by decanting the supernatant liquors. The residue was crystallized from methanol-ethylacetate to give 6-methyl-7,8-dimethoxy-1-phenyl-2,3,4,5-tetrahydro-1H-3-benzazepine hydrochloride, m.p. 223°–227°.

The dimethoxy compound (3.1 g, 0.0093 mole) was converted to the free base with alkali-methylene chloride. The organic layer was washed with water and dried, then was cooled to −15°, at which time 3 ml BBr3 were added. The reaction stirred 3½ hours at room temperature. The volatiles were stripped off and after cooling to −15°, methanol was added until the solid dissolved. The methanol was evaporated and the residue was dissolved in boiling water. The solution was treated with activated charcoal and filtered while hot. Crystallization of the hot solution gave 1.2 g of 6-methyl-7,8-dihydroxy-1-phenyl-2,3,4,5-tetrahydro-1H-3-benzazepine hydrobromide, m.p. 160°–163°. The base and methylsulfonate salt are prepared as described above.

EXAMPLE 9

Using N-alkylation or N-acylation procedures described in the previous two examples but using 6-propyl-7,8-dimethoxy-1-phenyl-2,3,4,5-tetrahydro-1H-3-benzazepine as a model compound the N-allyl, N-butyl, N-amyl, N-α-furylmethyl, N-α-thenyl, N-propargyl, N-phenacyl or N-2,2-dimethylallyl derivatives are prepared. Hydrolysis of the methoxy groups as described gives the more active 6-propyl-7,8-dihydroxy compounds.

EXAMPLE 10

A mixture of 100 g (0.8055 m) of 2,3-dihydroxytoluene, 325 ml of dimethylsulfate and 460 ml of 10% sodium hydroxide solution was taken to pH of 10 using 40% sodium hydroxide. The mixture was heated at reflux for ½ hour. An additional 50 ml of dimethylsulfate was added with 50 ml of 40% sodium hydroxide. Then the reaction mixture was heated at reflux for 40 minutes. This was repeated; then the mixture was cooled and extracted with ethyl ether. The combined ethereal extract was washed with water and alkali, dried and evaporated to give the desired 2,3-dimethoxytoluene in 98% yield.

This material, 149 g (0.97 m), was added to 557 ml of 1,2-dichloroethane and 150 ml of formaldehyde. The mixture was stirred while hydrogen chloride gas was added for 1½ hours. After a reflux period for 1 hour, the mixture was stirred at room temperature overnight. Hydrogen chloride was then again bubbled through the mixture for 1 hour. The mixture was heated at reflux for 3 hours. After cooling water was added. The aqueous layer was separated. The organic extracts were combined and washed with brine, dried and evaporated to give 2-methyl-3,4-dimethoxybenzyl chloride, m.p. 67°–68.5°.

This compound (80 g, 0.398 m) was taken into 300 ml of dimethylformamide and reacted with 22.43 g (0.457 m) of sodium cyanide at reflux for 1½ hours. Water was added to the mixture which was then extracted with ether. The washed and dried ethereal extracts were evaporated. The remaining oil was taken up in 300 ml of ether. The mixture was washed with 30 ml of conc. hydrochloric acid, shaken well then washed with brine, dried and evaporated. The resulting oil in 200 ml of dimethylformamide with 11 g of sodium cyanide was heated on a steam bath for 1 hour. Worked up as above to give 2-methyl-3,4-dimethoxyphenylacetonitrile, m.p. 60°–63°.

A mixture of 42 g (0.219 m) of the phenylacetonitrile 100 ml of tetrahydrofuran was mixed with 400 ml of 1 molar diborane in tetrahydrofuran then heated at reflux for 2½ hours. After cooling the mixture was quenched with 150 ml of methanol. After sitting overnight, the mixture was stripped. An excess of 10% hydrochloric acid was added followed by heating on the steambath for 2 hours. After cooling, ether was added. The mixture was stirred for ½ hour and evaporated. The remaining aqueous layer was made basic with 10% sodium hydroxide, extracted with ether which was dried and evaporated to give 2-methyl-3,4-dimethoxyphenethylamine.

The amine (23.3 g, 0.119 m) and methyl p-methoxymandelate (23.5 g, 0.119) were mixed together and heated on the steam bath overnight. Toluene was added to the oily mixture. The toluene was stripped away with the methanol byproduct to give the desired amide in quantitative yield.

This product (41 g, 0.1143 m) was dissolved in 508 ml of toluene and 169.7 ml of sodium aluminum bis(methoxyethoxy)-hydride (70% in toluene) was added slowly with stirring under nitrogen. The solution was then heated at 96° for 2 hours. After quenching with water and addition of 10% sodium hydroxide, the toluene layer was separated. The aqueous layer was extracted twice with methylene chloride. The organic extracts were combined and evaporated. The residue was taken up in methylene chloride. The extract was washed with water, dried and evaporated. The residue was recrystallized from ethanol-petroleum ether to give the desired N-[2-(2-methyl-3,4-dimethoxyphenyl)ethyl]-2-hydroxy-2-(p-methoxyphenyl)ethylamine, m.p. 128°–129°.

This compound (21.5 g, 0.063 m) was mixed with 161.25 ml of trifluoroacetic acid and 5.16 ml of sulfuric acid. The mixture was stirred at room temperature for 3½ hours. Anhydrous sodium acetate (23.3 g) was then added with cooling. The trifluoroacetic acid was evaporated. Water was added to the residue. The aqueous mixture was made basic with ammonium hydroxide with cooling. The mixture was extracted with ethyl acetate. The combined extract was washed with water, dried, evaporated, ether then added and evaporated to give 6-methyl-7,8-dimethoxy-1-(p-methoxyphenyl)-2,3,4,5-tetrahydro-1H-3-benzazepine, m.p. 100°–111°.

This base may be converted to any acid addition salt useful as an intermediate by reacting the base with an excess of the desired acid in an organic solvent as known to the art.

The trimethoxybenzazepine (1.5 g, 0.0046 m) was dissolved in 15.9 ml of methylene chloride and cooled. A solution of boron tribromide (2 M in methylene chloride) was added maintaining the temperature below 15°. The mixture was stirred at room temperature for 3 hours, cooled to −20° and 11.4 ml of methanol added. After returning to room temperature, the slurry was concentrated. The residue was triturated with ethyl acetate, cooled and a solid collected. The product, 6-methyl-7,8-dihydroxy-1-(p-hydroxyphenyl)-2,3,4,5-tetrahydro-1H-3-benzazepine hydrobromide, was recrystallized from methanol/ethyl acetate as the hemihydrate; m.p. 319°–320° (dec.).

The hydrobromide salt was dissolved in a minimum of methanol and neutralized with 50% sodium bicarbonate to give the solid free base. This was slurried in methanol with an excess of methanesulfonic acid to give the methanesulfonate salt. The hydrochloride and other pharmaceutically acceptable acid addition salts are made similarly.

The hydrochloride salt (2 g.) is dissolved in trifluoroacetic acid and 3.3 mole equivalents of isobutyryl chloride added slowly at room temperature. The mixture is heated at reflux for 1 hour, concentrated and the residue treated with an excess of ethereal hydrogen chloride. After evaporation the residue is triturated with ether/hexane to give 1-(p-isobutyryloxyphenyl)-7,8-diisobutyryloxy-6-methyl-2,3,4,5-tetrahydro-1H-3-benzazepine hydrochloride.

Other O-acyl derivatives can be made by substituting equimolar quantities of the appropriate acid chloride or anhydride in this procedure.

The critical ether splitting step of the reaction sequence may be also carried out with any agent known to split alkylaryl ethers such as hydrogen bromide or other acid agents such as concentrated hydrochloric acid under pressure, hydriodic acid or methanesulfonic acid-phosphorous pentoxide.

EXAMPLE 11

Using the chemical processes described in detail above and the following starting materials:

---

6-carbomethoxy-1-(p-chloro-m-methoxyphenyl)-7,8-dimethoxy-2,3,4,5-tetrahydro-1H-3-benzazepine
6-carbomethoxy-1-(p-methylthiophenyl)-7,8-dimethoxy-2,3,4,5-tetrahydro-1H-3-benzazepine
6-carbomethoxy-1-(o-methylphenyl)-7,8-dimethoxy-2,3,4,5-tetrahydro-1H-3-benzazepine
6-carbomethoxy-1-(m-methoxyphenyl)-7,8-dimethoxy-2,3,4,5-tetrahydro-1H-3-benzazepine
6-carbomethoxy-1-(p-ethoxyphenyl)-7,8-dimethoxy-2,3,4,5-tetrahydro-1H-3-benzazepine

--- gives the corresponding 6-methyl or 6-propyl compounds of this invention.

EXAMPLE 12

| Ingredients | Mg. per Capsule |
|---|---|
| 6-Methyl-7,8-dihydroxy-1-(p-hydroxyphenyl)-2,3,4,5-tetrahydro-1H-3-benzazepine | 50 mg. (free base) |

-continued

| Ingredients | Mg. per Capsule |
|---|---|
| (as an acid addition salt) | |
| Magnesium stearate | 2 |
| Lactose | 200 |

The above ingredients are thoroughly mixed and placed into hard gelatin capsules. Such capsules are administered orally to subjects in need of treatment from 2-5 times daily to induce dopaminergic activity at peripheral receptor sites, especially to induce antihypertensive activity. This active ingredient as the hydrobromide demonstrates anti-hypertensive activity in the dog at doses of from about 1-10 mg/kg orally.

EXAMPLE 13

| Ingredients | Mg. per Tablet |
|---|---|
| 6-Propyl-7,8-dihydroxy-1-phenyl-2,3,4,5-tetrahydro-1H-3-benzazepine hydrochloride | 150 (free base) |
| Corn starch | 30 |
| Polyvinyl pyrrolidone | 12 |
| Corn Starch | 16 |
| Magnesium stearate | 3 |

The first two ingredients are thoroughly mixed and granulated. The granules obtained are dried, mixed with the remaining corn starch and magnesium stearate, and compressed into tablets. The capsules are administered orally to subjects in need of treatment from 1-5 times daily to induce dopaminergic activity especially at peripheral centers to induce anti-hypertensive activity.

The capsules or tablets thusly prepared are administered orally to an animal or human requiring stimulation of dopamine receptors at either central or peripheral sites within the dose ranges set forth hereinabove. Similarly other biologically active compounds of Formula I and the illustrative examples can be formulated in the same manner to give pharmaceutical compositions useful in the methods of this invention based on the chemical characteristics and relative biological activity using the test methods outlined.

What is claimed is:

1. A compound of the structural formula:

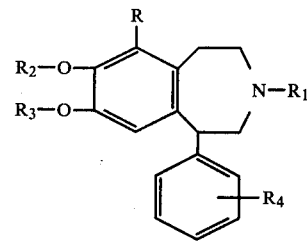

in which:
R is lower alkyl of 1-6 carbons;
$R_4$ is hydrogen or one substituent from the group consisting of trifluoromethyl, halo, methyl, methoxy, alkanoyloxy of 2-5 carbons, hydroxy or methylthio;
$R_2$ and $R_3$ are the same and are hydrogen, lower alkyl of 1-5 carbons, lower alkanoyl of 2-5 carbons, benzyl or, when taken together, methylene; and
$R_1$ is benzyl, phenethyl, lower alkanoyl of 1-5 carbons or, when $R_2$ and $R_3$ are other than hydrogen or alkanoyl, hydrogen; or pharmaceutically acceptable acid addition salts thereof.

2. A compound of claim 1 in which $R_2$ and $R_3$ are methyl, $R_1$ is hydrogen and $R_4$ is hydrogen or p-methoxy.

3. A compound of claim 1 being 6-methyl-7,8-dimethoxy-1-(p-methoxyphenyl)-2,3,4,5-tetrahydro-1H-3-benzazepine or one of its stable, pharmaceutically acceptable acid addition salts.

4. The compound of claim 3 as the base.

5. A compound of the formula:

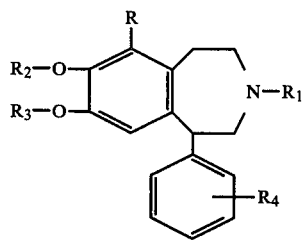

in which:
R is a α-hydroxyalkyl or α-chloroalkyl of 1-6 carbons;
$R_1$ is hydrogen, formyl or methyl;
$R_2$ and $R_3$ are the same and are methyl, benzyl or, when taken together, methylene; and
$R_4$ is hydrogen or one substituent from the group comprising trifluoromethyl, halo, methyl, methylthio or methoxy; or pharmaceutically acceptable acid addition salts thereof.

6. A compound of claim 5 in which R is chloromethyl.

7. A compound of claim 5 in which R is hydroxymethyl.

8. A compound of claim 5 in which R is α-hydroxypropyl.

9. A compound of claim 5 in which R is α-chloropropyl.

10. A compound of claim 5 in which R is chloromethyl, $R_2$ and $R_3$ are methyl, $R_1$ is formyl and $R_4$ is hydrogen.

* * * * *